United States Patent [19]
Gillies et al.

[11] Patent Number: 5,863,530
[45] Date of Patent: Jan. 26, 1999

[54] TREATING OPHTHALMIC FIBROSIS USING INTERFERON-α

[75] Inventors: Mark Cedric Gillies, Randwick; Nigel Morlet, Watsons Bay; Marc George Sarossy, Narrabundah, all of Australia

[73] Assignee: Spruson & Ferguson, Sydney, Australia

[21] Appl. No.: 726,861

[22] Filed: Oct. 4, 1996

Related U.S. Application Data

[63] Continuation of Ser. No. 211,655, filed as PCT/AU92/00541, Oct. 12, 1992, abandoned.

[30] Foreign Application Priority Data

Oct. 11, 1991 [AU] Australia ............................ PK 8865
Oct. 22, 1991 [AU] Australia ............................ PK 9080

[51] Int. Cl.⁶ .................................................. A61K 38/21
[52] U.S. Cl. ........................................ 424/85.7; 530/351
[58] Field of Search ............................ 424/85.7; 530/351

[56] References Cited

U.S. PATENT DOCUMENTS

| | | | |
|---|---|---|---|
| 4,507,281 | 3/1985 | Asculai et al. | 424/85 |
| 4,857,311 | 8/1989 | Domb et al. | 424/78 |
| 4,863,457 | 9/1989 | Lee | 604/89.1 |

FOREIGN PATENT DOCUMENTS

| | | |
|---|---|---|
| 77307/87 | 11/1989 | Australia . |
| 68292/87 | 9/1990 | Australia . |
| 68201/90 | 10/1992 | Australia . |
| 0082481 | 6/1983 | European Pat. Off. . |
| 03411/88 | 5/1988 | WIPO . |

OTHER PUBLICATIONS

Johnson–Wint, Ana. N.Y. Acad. Sci., vol. 548, pp. 167–173, 1988.
Gillies et al., Araefe's Archive for Clin & Exptal Ophthalmol., vol. 231, pp.118–121, 1993.
Duncan et al., J. Clin. Invest., vol. 79, pp. 1318–1324, 1987.
Berman et al., J. Am. Acad. Dermatol., vol. 21, pp. 694–702, 1989.
Duncan et al., Arch. Dermatol. Res., vol. 281, pp. 11–18, 1989.
Kahari et al., Biochim. et Biophysica Acta, vol. 968, pp. 45–50, 1988.
Dharma et al., Ophthalamic Surg., vol. 18(1), pp. 51–54, 1987.
Vegh et al., Ophthalamic Surg., vol. 17(2), pp. 103–105, 1987.
Jimenez et al., J. Clin. Invest., vol. 74, pp. 1112–1116, 1984.
Siebert et al., Plastic & Reconstr. Surg., vol. 85(4), pp. 495–502, 1990.
Garty DS, Kerr Muir MG, Marshall J. Excimer laser photorefractive keratectomy. 18 month follow up. Ophthalmology 1992;1209–1219.
Sher NA, Barak M, Daya S, De Marchi J, Tucci A, Hardten DR et al. Excimer laser photorefractive keratectomy in high myopia. A multicenter study. Arch Ophthalmol 1992; 110:935–943.
Gressel MG, Parrish RK II and Folberg R: 5–fluorouracil and glaucoma filtering surgery I. An animal model. Ophthalmology 1984; 91:378–83.
McDonald HR, Schatz II, Johnson RN. Introduction to epiretinal membranes. In Retina, Ryan SJ, ed., 2nd edition, St. Louis 1994, Mosby, pp. 1819–1825.
Blumenkraz MS, Claflin A and Hajek A: Selection of therapeutic agents for intraocular proliferative disease; cell cultire evaluation. Arch Ophthalmol 1984; 102:598–604.
Jimenez SA, Freundlich B and Rosenblom J. Selective inhibition of human diploid fibroblast collagen synthesis by interferons. J Clin Invest 1984; 74:1112–6.
Duncan MR and Berman B. Persistence of a reduced collagen–producing phenotype is cultured scleroderma fibroblasts after short–term exposure to interferons. J Clin Invest 1987; 79:1318–24.
Low SQ, Kitada S, Lee DA. Interferon–γ inhibits collagen synthesis by human Tenon's capsule fibroblasts in vitro Invest Ophthalmol Vis Sci 1991; 32:2964–9.

*Primary Examiner*—Chhaya D. Sayala
*Attorney, Agent, or Firm*—Morgan & Finnegan, LLP

[57] ABSTRACT

The present invention relates to the use of topical interferon-α for the treatment of various forms of fibrosis in and around the eye arising from various ophthalmic diseases and procedures. Specifically the invention relates to alleviation of corneal scarring after laser photoablative refractive keratectomy (PRK). It aslo relates to the alleviation of posterior (lens) capsular opacification after extracapsular cataract surgery with lens implant; the alleviation of wound scarring following glaucoma filtration surgery. Interferon-α may also be used to coat the lens implant prior to or during implantation. It may also possibly be injected into the eye during eye surgery for inhibiting posterior capsule opacification after cataract surgery and in addition may be injected into the vitreous body to prevent retinal fibrosis and proliferative vitreo-retinopathy, and injected subconjunctivally to inhibit fibrosis and scarring following glaucoma filtration surgery,.

10 Claims, No Drawings

TREATING OPHTHALMIC FIBROSIS USING INTERFERON-α

This is a continuation of application Ser. No. 08/211,655, filed as PCT/AU92/00541, Oct. 12, 1992, abandoned.

TECHNICAL FIELD

The present invention relates to the use of topical interferon-α for the treatment of various forms of fibrosis in and around the eye arising from various ophthalmic diseases and procedures. Specifically the invention relates to alleviation of corneal scarring after laser photoablative refractive keratectomy (PRK). It also relates to the alleviation of posterior (lens) capsular opacification after extracapsular cataract surgery with lens implant; the alleviation of wound scarring following glaucoma filtration surgery. Interferon-α may also be used to coat the lens implant prior to or during implantation. It may also possibly be injected into the eye during eye surgery for inhibiting posterior capsule opacification after cataract surgery and in addition may be injected into the vitreous body to prevent retinal fibrosis and proliferative vitreo-retinopathy, and injected subconjunctivally to inhibit fibrosis and scarring following glaucoma filtration surgery.

BACKGROUND ART

In the field of ophthalmic surgery, it is known to use excimer laser photoablative refractive keratectomy to sculpt the cornea of the eye in order to relieve refractive errors (e.g. myopia) and a number of corneal conditions and diseases. Specifically, the 193 nm argon fluoride excimer laser is able to discretely remove corneal tissue by photoablation without thermal damage to surrounding tissue.

Of major concern is the activation of the stromal keratocytes when a wound is made to the stroma. As is well known, the basic response of wounded tissue is to repair the defect and therefore the ophthalmic surgeon when using this technique is confronted with alteration to the biochemistry, morphologic features and tissue function unpredictability brought about by the wound itself and the healing phenomenon.

Therefore, even though excimer laser ablation of corneal tissue appears to be an efficient method of removing tissue with minimal damage to adjacent areas, nevertheless the healing process does not always lead to the preservation of transparent corneal tissue.

Previous methods of overcoming this problem have been: application of topical steroids such as prednisolone, prednisolone acetate, prednisolone sodium phosphate, fluoromethalone, fluoromethalone acetate, hydromesterone, dexamethasone, and dexamethasone alcohol. Other compounds tested have been idoxuridine, collagen crosslinkage inhibitors and mitomycin C.

It is an object of this invention to ameliorate the known disadvantages of present techniques when dealing with the wound repair mechanism following photoablative refractive keratectomy.

Interferons are a heterogeneous group of proteins that can inhibit many aspects of the fibrotic response. Originally identified by their well known ability to interfere with the production of viral RNA and protein, they also exert anticellular activities generally considered to be inhibitory, which maybe due to their ability to inhibit the c-myc proto-oncogene. Type I interferon (viral interferon, interferon-α and -β) is produced in response to viral infection, and type II (immune interferon, interferon-γ) in response to specific antigens or mitogens. Of the different classes, α-interferon is secreted by leukocytes, β- by fibroblasts and γ- by stimulated lymphocytes. Interferons, particularly interferon-α, have been successfully used in humans for twenty years for the treatment of systemic malignancy.

Considerable interest has recently been shown in the potential of interferon as a treatment for such fibrotic diseases as systemic sclerosis, pulmonary fibrosis and keloid. Fibroblasts are stimulated to produce interferons by many cytokines that mediate wound healing, such as interleukin-1-(IL-1), platelet derived growth factor (PDGF) and tumour necrosis factor (TNF). Interferons inhibit fibroblast chemotaxis and proliferation as well as collagen production, the latter synergistically with TNF-α. Intraperitoneally implanted foreign bodies in mice suffered less encapsulation in the presence of interferon-γ, the capsules having a reduced collagen content. Fibroblast glycosaminoglycan production is inhibited by interferon-α, while collagenase production is increased. This deactivation of activated fibroblasts can persist for a long time after a brief exposure to interferon. Of the different types of interferon, the α- and β-subclasses exhibit a broader antifibrotic spectrum.

The present inventors have recently demonstrated that interferon-α inhibits foetal calf serum and platelet derived growth factor induced proliferation of human tenon's capsule fibroblasts in vitro. They suggest that interferons may prove to be of benefit in the treatment of fibrosis following PRK in particular, and of ocular fibrosis in general.

DISCLOSURE OF THE INVENTION

According to a first form of this invention, there is provided a method for the treatment of corneal scarring in a patient requiring such treatment, comprising administering to the cornea of said patient an effective amount of interferon-α or a pharmaceutical composition for the treatment of corneal scarring in a patient comprising interferon-α together with a pharmaceutically acceptable carrier, diluent and/or excipient.

According to a second form of this invention, there is provided a method for inhibiting opacification of the posterior capsule after extracapsular cataract surgery, in a patient requiring such treatment, comprising administering to the lens capsule of said patient an effective amount of interferon-α or a pharmaceutical composition for this method comprising interferon-α together with a pharmaceutically acceptable carrier, diluent and/or excipient.

According to a third form of this invention, there is provided a method for inhibiting wound fibrosis and scarring after glaucoma filtration surgery, in a patient requiring such treatment, comprising administering to the subconjunctival space of said patient an effective amount of interferon-α or a pharmaceutical composition for this method comprising interferon-α together with a pharmaceutically acceptable carrier, diluent and/or excipient.

According to a fourth form of this invention, there is provided a method for inhibiting formation of pre-retinal membranes and proliferative vitreo-retinopathy following retinal detachment surgery and/or vitrectomy, following trauma, and as a result of retinal vascular disease (including diabetes, thalassaemia and retinal vein occlusion) in a patient requiring such treatment, comprising administering to the vitreous body or retina of said patient an effective amount of interferon-α or a pharmaceutical composition for this method comprising interferon-α together with a pharmaceutically acceptable carrier, diluent and/or excipient.

Interferon-α 2A, interferon-α 2B or interferon-α 2C or any other type of interferon-α may be used in this invention.

The invention also provides novel protein formulations in which the carrier or diluent is a bioerodable polymer, e.g. a polymer ester (polyanhydrine), which may be a copolymer of sebacic acid and bis paracarboxyphenoxybutane; or a poly(ortho) ester.

The method of this invention inhibits the scarring response following a variety of corneal procedures such as photoablative refractive keratectomy; lamellar keratoplasty; lamellar keratectomy; epikeratoplasty; removal of pterygium and keratomileusis.

Typically, the patient on whom the methods of this invention are used is a human. However, the methods would also be able to be used on other mammals.

The methods of this invention may also inhibit scarring after chemical damage to conjunctiva and cornea and may also prevent scarring in pathological conditions such as ocular pemphigoid and Stevensjohnson's syndrome, Simplex & Zoster keratitis. It may also inhibit fibrosis in thyroid eye disease, orbital psuedo-tumour and ocular myositis.

Preparation of topical composition drops are made up from Intron A powder (Schering-Plough) or Roferon-A (Roche) to a solution of $1\times10^6$ IU/mL.

Formulation of Intron A is as follows:

α-2b interferon solution

Dibasic sodium phosphate, anhydrous, USP

Monosodium phosphate, monohydrate, USP

Glycine, ph. eur.

Human albumin solution, ph. eur.

Water for injection, ph. eur.

Drops base may be hypromellose or polyvinyl alcohol for dilution to $10^6$ IU/mL.

The composition of the present invention may be administered topically as a solution, ointment, or within a collagen shield or similar dissolving corneal contact protective dressing containing conventional, non-toxic, pharmaceutically acceptable carriers, diluents and/or excipients as desired, or by direct injection.

The dosage range of interferon-α may be between about 50,000 and $50\times10^6$ IU and may be between about $1\times10^6$ to $20\times10^6$ IU/mL. Preferably the dosage is between about $1\times10^6$ and about $10\times10^6$ IU/mL. The interferon-α may be administered in 50 μL drops, four times a day for six weeks; or preferably two times a day for one week. Interferon-α may also be administered two times a day for three days or one drop hourly for three days. This dosage range is applicable to the first, second and third embodiments of the invention.

When applied according to the fourth embodiment the interferon-α is given by intravitreal injection within the range of 50,000 to $5.0\times10^6$ IU/0.1 mL.

The compositions of this invention may also contain a slow release polymer.

The pharmaceutically acceptable carriers, diluents and/or excipients are those well known in the art of ophthalmic surgery and comprise the following: hydroxyethyl cellulose, hypromellose, polyvinyl alcohol, gelatin, polyquad, dextran, castor oil or other vegetable oil e.g. sesame, inert soft white paraffin, liquid paraffin, anhydrous lanolin, sodium hyalusonate, methyl cellulose, potassium sorbate, polysorbate; or sodium chloride, sodium phosphate, buffers hydrochloric acid bicarbonate, Na citrate (citric acid) boric acid in purified water. They may also be biodegradable polymer esters (polyanhydrines) e.g. sebacic acid and bis paracarboxyphenoxybutane, which are employed in the novel formulations of the invention.

The compositions may also contain preservatives and antiseptics such as: thiomersal, phenyl mercuric acetate, benzylalkonium chloride, disodium edetate, sodium metabisulfite, polymercuric nitrate, chlorobutol, hyloxapol, povidone, propyl hydroxy benzoate, methyl hydroxy benzoate.

It is preferable that the composition of this invention be applied to the cornea immediately following photoablative refractive keratectomy. As a drop, ointment or collagen shield etc. Where the interferon is applied as a drop, it is preferably to treat the eye thus, four to eight times a day for up to about 6 weeks.

The corneal response may be modified by the pre-treatment with interferon α drops before PRK. It may also be modified by pre-treatment with steroid drops.

The interferon-α may be prepared from natural sources or may be prepared by recombinant DNA techniques. All of these techniques would be well known to one skilled in this art.

BEST MODE AND OTHER MODES FOR CARRYING OUT THE INVENTION

An effective amount of interferon-α-2b to prevent corneal scarring after photoablative refractive keratectomy is administered topically to the cornea which has been subjected to this procedure.

The present invention will now be described with reference to the following examples which should not be construed as limiting on the scope thereof.

EXAMPLE 1

Preparation of interferon α-2B topical composition

Preparation of topical composition drops are made up from Intron A powder (Schering-Plough) to a solution of $1\times10^6$ IU/mL.

Formulation of Intron A is as follows:

α-2b interferon solution

Dibasic sodium phosphate, anhydrous, USP

Monosodium phosphate, monohydrate, USP

Glycine, ph. eur.

Human albumin solution, ph. eur.

Water for injection, ph. eur.

The drops base is hypromellose or polyvinyl alcohol for dilution to $10^6$ IU/mL.

EXAMPLE 2

The composition of this invention is applied to the cornea immediately following photoablative refractive keratectomy, As a drop, ointment or collagen shield etc. Where the interferon is applied as a drop, it is preferable to treat the eye thus, four times a day for up to about 6 weeks.

The corneal response may be modified by the pre-treatment with interferon-α-2b drops before PRK. It may also be modified by pre-treatment with steroid drops.

INDUSTRIAL APPLICABILITY

It should be clear that the method of treatment of this invention will find wide use in the veterinary and medical fields.

The foregoing describes only some embodiments of the present invention and modifications obvious to those skilled

REFERENCES

Gipson I K (1990) Archives of Opthalmology 108 1539.
Cintron C (1990) Archives of Opthalmology 108 1540.
Binder P S (1990) Archives of Opthalmology 108 1541.

We claim:

1. A method for inhibiting formation of pre-retinal membranes and proliferative vitreo-retinopathy following retinal detachment surgery and/or vitrectomy, following trauma, and as a result of retinal vascular disease in a patient requiring such treatment, comprising administering to the vitreous body or retina of said patient an effective amount of interferon-α or a pharmaceutical composition thereof.

2. The method according to claim 1 wherein the interferon-α is given by intravitreal injection within the range of about 50,000 to $5.0 \times 10^6$ IU/0.1 mL.

3. A method for inhibiting corneal hazing resulting from laser photoablative keratectomy by administering to a mammal, undergoing said surgery, a pharmaceutical composition comprising interferon-α and a carrier applied at a dosage of between 50,000 and $50 \times 10^6$ IU/mL.

4. A method according to claim 3 wherein the dose level is between $1 \times 10^6$ and $20 \times 10^6$ IU/mL.

5. A method according to claim 3 wherein the dose level is between $1 \times 10^6$ and $10 \times 10^6$ IU/mL.

6. A method according to claim 3 wherein the interferon-α is interferon-α-2A.

7. A method according to claim 3 wherein the interferon-α is interferon-α-2B.

8. A method according to claim 3 wherein the interferon-α is interferon-α-2C.

9. A method according to claim 3 wherein the carrier is a bioerodible polymer selected from the group consisting of a polyanhydride ester and a poly(ortho)ester.

10. A method according to claim 9 wherein the bioerodible polymer is a copolymer of sebacic acid and bisparacarboxyphenoxybutane.

* * * * *

UNITED STATES PATENT AND TRADEMARK OFFICE
CERTIFICATE OF CORRECTION

PATENT NO. : 5,863,530
DATED : January 26, 1999
INVENTOR(S) : Mark C. Gillies, et. al.

It is certified that error appears in the above-indentified patent and that said Letters Patent is hereby corrected as shown below:

Title page, item [73], Assignee: delete "Spruson & Ferguson, Sydney Australia"

Signed and Sealed this

Thirteenth Day of March, 2001

Attest:

NICHOLAS P. GODICI

Attesting Officer

Acting Director of the United States Patent and Trademark Office